US00RE48023E

(19) United States
(12) Reissued Patent
Kim et al.

(10) Patent Number: US RE48,023 E
(45) Date of Reissued Patent: Jun. 2, 2020

(54) METHOD FOR TREATING VASCULAR-RELATED DISEASE

(71) Applicant: EYEGENE INC., Seoul (KR)

(72) Inventors: Doo-Sik Kim, Seoul (KR); Yang-Je Cho, Seoul (KR); Won-Il Yoo, Gyeonggi-do (KR); Oh-Woong Kwon, Gyeonggi-do (KR); Jin-Wook Jang, Seoul (KR); Hyeong-Joon Lim, Gyeonggi-do (KR); Soo-Mee Kwon, Seoul (KR)

(73) Assignee: EYEGENE INC., Seoul (KR)

(21) Appl. No.: 15/158,437

(22) Filed: May 18, 2016

Related U.S. Patent Documents

Reissue of:
(64) Patent No.: 9,101,581
Issued: Aug. 11, 2015
Appl. No.: 14/044,692
Filed: Oct. 2, 2013

U.S. Applications:
(63) Continuation of application No. 12/087,763, filed on Oct. 27, 2008, now Pat. No. 9,101,581, and a continuation of application No. 12/087,763, filed as application No. PCT/KR2007/000030 on Jan. 19, 2007, now abandoned.

(30) Foreign Application Priority Data

Jan. 19, 2006 (KR) ..... 10-2006-0005975
Aug. 21, 2006 (KR) ..... 2007000330

(51) Int. Cl.
*A61K 38/16* (2006.01)
*A61K 35/12* (2015.01)
*A61K 35/15* (2015.01)
*A61K 35/17* (2015.01)

(52) U.S. Cl.
CPC ..... *A61K 38/16* (2013.01); *A61K 35/12* (2013.01); *A61K 35/15* (2013.01); *A61K 35/17* (2013.01)

(58) Field of Classification Search
CPC ..... A61K 35/12
See application file for complete search history.

(56) References Cited

U.S. PATENT DOCUMENTS

| | | | | |
|---|---|---|---|---|
| 5,629,294 | A | 5/1997 | diZerega et al. | |
| 6,818,617 | B1 | 11/2004 | Niewiarowski et al. | |
| 7,074,408 | B2 * | 7/2006 | Fanslow, III | C07K 14/705 424/185.1 |
| 7,971,592 | B2 | 7/2011 | Ochi | |
| 2002/0042368 | A1 * | 4/2002 | Fanslow et al. | 514/12 |
| 2004/0133271 | A1 | 7/2004 | Jang | |
| 2004/0171549 | A1 | 9/2004 | Trochon et al. | |

OTHER PUBLICATIONS

E. Chavakis et al., Kinetics of integrin expression in the mouse model of proliferative retinopathy and success of secondary intervention with cyclic RGD peptides, Diabetologia 45: 262-267, 2002.
Lo-Chun Au et al., Nucleotide sequence of a full-length cDNA encoding a common precursor of platelet aggregation inhibitor and hemorrhagic protein from *Calloselasma rhodostoma* venom, Biochimica et Biophysica Acta, 1173 (1993) 243-245.

* cited by examiner

*Primary Examiner* — Padmashri Ponnaluri
(74) *Attorney, Agent, or Firm* — Harness, Dickey & Pierce, P.L.C.

(57) ABSTRACT

A method for treating a vascular-related disease in a subject in need thereof, includes administering to the subject a peptide having a sequence Xaa-Gly-Asp. The peptide may have a sequence of SEQ ID NOS: 1, 2, 4, 6 to 10. The vascular-related disease may be edema and/or ischemia caused by blood leakage of blood vessel walls, damages of blood vessels or abnormal angiogenesis.

19 Claims, 13 Drawing Sheets

Specification includes a Sequence Listing.

control

RGD control

RGD

METHOD FOR TREATING VASCULAR-RELATED DISEASE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

This application is a [divisional] *continuation* application of application Ser. No. 12/087,763 filed Oct, 27, 2008, which is the National Stage of international Application No. PCT/KR2007/000330 with an international Filing Date of Jan. 19, 2007, which claims the benefit of Korean patent application No. 10-2006-0005975 filed in the Korean intellectual Property Office on Jan. 19, 2006 and the benefit of international Application No. PCT/KR2006/003283 with an International Filing Date of Aug. 21, 2006, the entire contents of which are incorporated herein by reference.

TECHNICAL FIELD

The present invention relates to a compound for treating edema, ischemia, and related vascular diseases by stabilizing blood vessel walls to form and maintain new blood vessels, thereby preventing blood leakage and helping growth of normal blood vessels. More particularly, the present invention relates to a composition capable of being used as a therapeutic agent for treating vascular-related diseases by forming and maintaining normal blood vessels to prevent blood leakage using peptides and/or stem cells comprising a basic amino acid-Gly-Asp sequence.

BACKGROUND ART

As one of the vascular diseases, ischemia is so called as a local blood deficiency in which blood supply into tissues is stanched due to vessel stenosis, contraction, thrombus, embolism, etc., resulting in cell damages.

In 1961, it was reported by Majno and Palade that blood is leaked since gaps are formed between vascular endothelial cells of venules by inflammations which are caused by hiatamine bradykinin and serotonin (Majno G., Palade G. E., J. Biophys. Biochem. Cytol. 11:571-605 (1961); Majno G., Palade G. E., Schoetl G. I., J. Biophys. Biochem. Cytol. 11:607-625 (1961)).

It has been known that the gaps between the vascular endothelial cells are generated after the exposure to inflammation-inducing agents as well as various cytokines (Claudio L. et al., Lab Invest. 70:850-861 (1994); Wu N. Z., Baldwin A. L. Am. J. Physiol. 262:H1238-1247 (1992)), proteases (Volkl K. P., Dieriehs R. Thromb. Res. 42:11-20 (1986)), and mild heat injuries (Clough G. et al., J. Physiol. 395:99-114 (1988)). Also, this phenomenon was found in various kinds of cancers (Hobbs S. K. et al., Proc. Natl. Acad. Sci. USA 95:4607-4612 (1998); Roberts W. G. et al., Am. J. Pathol. 153:807-830 (1998); Nishio S. et al., Acta. Neuropathol. (Berl) 59:1-10 (1983)). In addition to the cancers, the phenomenon was found in human asthma (Laitinen A., Laitiene L. A. Allergy Proc. 15:323-328 (1994)), pigmentosa urticaria (Ludatscer R. M. Microrasc. Res. 31:345-355 (1986)), rheumatism (Schumacher H. R. Jr. Ann. N.Y. Acad. Sci. 256:39-64 (1975)), etc.

Blood vessel has various characteristics, for example a characteristic associated with modification of blood vessels including vasodilation and angiogenesis in the case of chronic inflammations. At this time, it was found that the blood vessels are deformed into a shape where they have abnormal characteristics rather than normal characteristics, and diameters of the blood vessels are increased and immune responses to von Willebrand factor and P-selectin are enhanced in a murine chronic airway inflammation model. As described above, it was revealed that the deformed blood vessels are weak in the response of immune mediators, compared to those of normal mice.

For this reason, there have been many attempts to develop substances for suppressing or reducing growth of abnormal blood vessels or blood leakage. It was reported that mystixins are synthetic peptides that inhibit plasma leakage without preventing gaps from being generated in vascular endothelial cells (Blauk P., et al., J. Pharmacol. Exp. Ther., 284: 693-699 (1998)). Also, it has been known that β-2-adrenergic receptor agonist formoterol reduces blood leakage if the gap formation is suppressed in vascular endothelial cells (Blank P. and McDonald D. M., Am. J. Physiol., 266:L461-468 (1994)).

There have been attempts to develop substances that cause morphological changes in blood vessels, and angiopoietin has stood as one of the substances in the spotlight. The angiopointin-1 functions to stabilize blood vessels (Thurston G. et al., Nat. Med. 6 (4): 460-3 (2000)) and also stabilize angiogenesis of VEGF, resulting in suppression of blood leakage. It has been reported that this mechanism is used to treat diseases including retinopathy caused by peripheral vascular disease in chronic diabetes, retinopathy of prematurity caused by angiodysplasia, etc. (Joussen A. M. et al., Am. J. Pathol. 160 (5): 1683-93 (2002)). However, recombinant angiopoietin-1 should not be directly used to treat diseases since it has problems such as stability, solubility or the like, and therefore, as an alternative, there have been attempts to develop alternative substances havingan angiopoietin-1 activity (Koh G. Y. et al., Exp. Mol. Med. 34 (1): 1-11 (2002)). In the recent years, it was known that platelet is activated to release angiopoietin-1 in order to stabilize newly formed blood vessels in angiogenesis (Huang et al., Blood 95:1993-1999 (2000)). Also, it was reported that thrombin is associated with the activation of the platelet to release angiopoietin-1 from the platelet (Li et al., Throm. Haemost. 85:204-206 (2001)). However, the thrombin functions not to release only angiopoietin-1 to stabilize blood vessels but be a part of phenomena appearing with coagulation of the platelet. Therefore, it is difficult to use the thrombin to control the release of angiopoictin-1, and it may be anticipated that there are side effects caused by the blood coagulation. In addition, there have been attempts to search for compounds inducing secretion of angiopoietin-1, but there is no report of the compounds in the art.

It has been known that conventional peptides including RGD and KGD motifs inhibit angiogenesis (Victor I. R. and Michael S. G. Prostate 39:108-118 (1999); Yohei M. et. al., J. of Biological Chemistry 276:3:31959-31968 (2001)). It was reported that the above-mentioned effect is exhibited when the peptides including RGD and KGD motifs bind to $\alpha v\beta 3$ integrin of vascular endothelial cells (Pasqualini R. et al., Nat. Biotechnol. 15 (6): 542-6 (1997)). Generally, the integrin is a cell-to-cell or cell-to-substrate mediator which is essential to growth of the vascular endothelial cells (Brian P. Eliceiri, Circ. Res. 89:1104-1110 (2001)). Therefore, disinfegrins that bind to the integrin to inhibit the roles of the integrin includes a RGD motif or a KGD motif that is mainly one of structural motifs of fibrinogen. For this purpose, there have been attempts to study how many peptides including RGD and KGD motifs bind to integrin to inhibit angiogenesis by interrupting growth and movement of vascular endothelial cells. Also, angiogenesis in tissues needs integrin αvβ3, and RGD and KGD motif-comprising peptides inhibiting the angiogenesis are used to inhibit angiogenesis thereby to interrupt blood supply by suppressing formation of new blood vessels and killing the newly formed blood vessels, as disclosed in International Patent Publication No. WO 95/25543 (1995), U.S. Pat. No. 5,766,591 (1998) discloses that growth of solid cancers is suppressed by inhibiting angiogenesis using RGD and KGD motif-comprising peptides as an integrin αvβ3 antagonist.

In the recent years, in order to treat heart diseases, there have been attempts to develop an inhibitor which binds to αIIbβ3 is integrin using fibrinogen as a ligand and inhibits the integrin (Topol et al., Lancet 353:227-231 (1999); Lellovits et at N. Eng. J. Med. 23: 15530-1559 (1995); Coder B S J. Clin. Invest. 99: 1467-1471)). However, it was reported that these attempts were not successful (O'Neill et al., N. Eng. J. Med. 342: 1316-1324 (2000); Cannon et al., Circulation 102: 149-156 (2000)). This is why peptides comprising RGD and KGD motifs functions to activate integrin in a concentration-dependent manner to induce activation of platelet, as well as to bind to existing integrin to inhibit the activation of integrin (Karlheinz et al., Throm. Res. 103: S21-27 (2001); Karlheinz et al., Blood 92 (9); 3240-3249 (1998)). Ligand-induced binding sites (LIBS) are present in the integrin. At this time, if the RGD and KGD peptides bind to the integrin, conformational changes of the integrin are induced used to exposed the LIBSs, and then ligands bind to the exposed LIBSs to activate platelet (Leisner et al., J. Biol. Chem. 274:12945-12949 (1999). It was reported that this activation of the platelet is induced in a low concentration but not in a high concentration. If the RGD and KGD motifs may stabilize the platelet in this manner, cytokines (for example, angiopoietin-1), secreted in activating the platelet, may contribute to increasing and stabilizing, rather than inhibiting, the blood vessel formation.

In the present invention, very different results were obtained that the RGD and KGD motif-comprising peptides dose not suppress blood supply by inhibiting and killing newly formed blood vessels, as described above, but facilitates blood supplies by contributing to the normal blood vessel formation and stabilizing the formed blood vessels to inhibit blood leakage. It was confirmed that the RGD and KGD motif-comprising peptides are not effective in directly reacting to integrin to inhibit angiogenesis but effective in treating and preventing an injury, a burn, bedsore and chronic ulcer, as well as preventing the blood leakage to treat intraocular diseases such as diabetic retinopathy, retinopathy of prematurity, age-related macular degeneration, etc., and forming and stabilizing normal blood vessel while suppressing abnormal angiogenesis in a secondary reaction the RGD and KGD motif-comprising peptides.

Also, in the case of alopecia or trichopoliosis, hair follicle in contact with blood vessels serves to form medulla, cortex, cuticle, which constitute a hair. At this time, if the smooth blood supply to hair follicle is not facilitated by the blood leakage in the abnormal blood vessels, the hair follicle, namely hair, is not formed, and also trichopoliosis where hair colors are changed to a white color is induced since melanosome is not normally formed in hair root cell constituting hair shaft.

It is anticipated that the composition provided in the present invention is effective also in treating and preventing these conditions since the composition facilitates the blood supply by stabilizing the blood vessel formation to suppress the blood leakage. In addition, it is anticipated that the composition is effective also in treating and preventing obesity-associated cardiovascular diseases, a vascular therapeutic agent for artificial skin and transplantation, ischemia, etc.

As another alternative, there is a method for newly forming normal blood vessels in a stage of losing blood vessels and preventing diseases occurring in a later stage. In the method, there have been attempts to treat oculovascular diseases using stem cells. It was known that bone marrow includes endothelial precursor cells (EPCs) that can form new blood vessels, and it was also reported that bone marrow-derived heamatopoietic stem cells (HSCs) act as endothelial precursor cells when they are administered in order to facilitate the retinal angiogenesis (Grant M. B. et al., Nature Med 8:607-612 (2002)). The endothelial precursor cells may be differentiated into circulating EPCs (cEPCs), which are associated with angiogenesis. In addition, it was reported that heamatopoietic stem cells (HSCs), heamatopoietic progenitor cells (HPCs) and the like are associated with forming and sustaining new blood vessels (Rafii S. et al., Nature Med. 9:7027-712 (2003)). For a therapeutic purpose, it was reported that heamatopoietic stem cells act as a progenitor for forming retinal blood vessels by administering bone marrow-derived heamatopoietic stem cells into vitreous cavities of mouse eyes (Otani A. et al., Nature Med 9:1004-1010 (2002)). In addition to the heamatopoietic stem cells, various kinds of stem cells such as embryonic stem cells, mesenchymal stem cells, etc have been reported. The heamatopoietic stem cells do not trigger immune rejection in the case of autologous transplantation but triggers immune rejection in the case of allogeneic transplantation or xenotransplantation. Accordingly, the above method remains to be solved.

SUMMARY

Accordingly, the present invention is designed to solve the problems of the prior art, and therefore it is an object of the present invention to provide a therapeutic agent capable of inducing normal angiogenesis using peptides comprising a specific sequence.

In order to accomplish the above object, the present invention provides a pharmaceutical composition for treating edema and/or vascular-related diseases, including a peptide comprising a sequence Xaa-Gly-Asp as an effective component.

According to the present invention, the amino acid Xaa of the peptide is preferably Arg or Lys, and the peptide sequence is the most preferably set forth in SEQ ID NO: 1 or SEQ ID NO: 2.

According to the present invention, the peptide sequence also includes one peptide sequence selected from the group consisting of SEQ ID NO: 4, and SEQ ID NO: 6 to SEQ ID NO: 10.

In the present invention, the vascular-related diseases includes diseases, but is not particularly limited to, selected from the group consisting of diabetic retinopathy, retinopathy of prematurity, age-related macular degeneration, glaucoma, diabetic foot ulcer, pulmonary hypertension, ischemic myocardium, ischemic brain diseases, skin flap survival, heart failure, acute hindlimb ischemia, an injury, a burn, bedsore, chronic ulcer, alopecia or trichopoliosis in normal capillary formation, obesity-associated cardiovascular diseases, a vascular therapeutic agent for artificial skin and transplantation, and ischaemia.

Also, it is anticipated that the peptides comprising RGD and KGD motifs are effective in treating alopecia or trichopoliosis in normal capillary formation or obesity-associated cardiovascular diseases, as well as in healing an injury caused by edema and ischemia or a burn and treating and preventing bedsore and chronic ulcer.

Also, the peptide of the present invention induces secretion of angiopoietin-1.

Also, it was reported that COMP-Ang1 as a modified angiopoietin-1 functions to protect vascular endothelial cells of the kidney in a unilateral ureteral obstruction (UUO) model to suppress inflammations, thereby preventing infiltration of monocyte or macrophage, and to reduce an amount of TGF-β1 in the tissue to suppress phosphorylation of Smad 2/3 and activate Smad 7 to reduce fibrosis in the kidney (Kim et al., J. Am. Soc. Nephrol. 17: 2474-2483 (2006)). It was revealed that the aniopoietin-1 might be used as a therapeutic agent that can specifically react to vascular endothelial cells in renal fibrosis to treat renal diseases. It is considered that a polypeptide comprising a RGD or KGD motif according to the present invention may be useful to treat the renal diseases by indirectly inducing in vivo release of angiopoietin-1.

The polypeptide comprising a sequence Xaa-Gly-Asp of the present invention may be used alone, but more effective if it is used in combination with VEGF (Benest et al., Microcirculation, 13:423-437 (2006)) or bFGF.

Also, the present invention provides a pharmaceutical composition for treating vascular-related diseases, the composition further including a stem cell in addition to the peptide.

According to the present invention, the stem cell is preferably a stem cell having at least an ability to differentiate into vascular endothelial cells, for example an embryonic stem cell, a mesenchymal stem cell and a hematopoietic stem cell.

Also, the vascular-related diseases that may be treated with the stem cell-comprising composition of the present invention are, but not particularly limited to, selected from the group consisting of pulmonary hypertension, ischemic myocardium, skin flap survival, heart failure, acute hindlimb ischemia and ocular diseases.

The peptide having an ability to treat diseases such as ischemia described in the present invention includes a peptide comprising a sequence Xaa-Gly-Asp or its fragments and derivatives having the same functional ability, and, if a stem cell is used to treat the diseases, the stem cell is preferably used together with the polypeptide comprising a sequence Xaa-Gly-Asp.

The angiogenesis-related diseases that may be treated or prevented by the protein and the stem cell of the present invention is preferably diseases that may be treated using a therapeutic mechanism for inducing secretion of angiopoietin-1 to stabilize newly formed blood vessels, the diseases being selected from the group consisting of pulmonary hypertension (Ann Thorac Surg 2004 February 77 (2) 449-56), ischemic myocardium (with VEGF; Biochem Biophys Res Commun. 2003 Oct. 24; 310 (3):1002-9), skin flap survival (Microsurgery. 2003; 23 (4):374-80), heart failure (Cold Spring Harb Symp Quant Biol 2002; 67:417-27), acute hindlimb ischemia (with VEGF; Life Sci 2003 Jun. 20; 73 (5):563-79), etc., and the ocular diseases are more preferred.

The ocular diseases, which are applicable in the present invention, are particularly retinopathy of prematurity, diabetic retinopathy, glaucoma, etc.

The pharmaceutically available composition of the present invention includes, for example, an available diluent, an additive or a carrier.

The pharmaceutically available composition of the present invention includes the peptide together with a pharmaceutically available composition suitable for delivery or administration to in vivo or ex vivo tissues or organs.

The pharmaceutical composition may include the peptide and/or the proteins in forms of free acids or bases or pharmaceutically available salts since the peptide and/or the proteins may contain acidic and/or basic terminuses and/or side chains. The pharmaceutically available salts may includes suitable acids to form a base with the peptide and/or the proteins of the present invention, the suitable acids being selected from the group consisting of inorganic acids such as hydrochloric acid, hydrobromic acid, perchloric acid, nitric acid, thiocyanic acid, sulfuric acid, phosphoric acid and derivatives thereof; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid, sulfanilic acid and derivatives thereof. The suitable bases to form a base with a target protein may include, for example, inorganic bases such as sodium hydroxide, ammonium hydroxide, potassium hydroxide, and derivatives thereof, and organic bases such as mono-, di- and tri-alkylamine, (for example, triethylamine, diisopropylamine, methylamine dimethylamine, and derivatives thereof) and optionally substituted ethanolamines (for example, ethanolamine, diethanolamine, and derivatives thereof).

The pharmaceutical composition may be administered in various routes including, but is not limited to, parenteral, enteral, topical administrations or inhalations. The parenteral administration means any administration that is not administered through a digestive tract, including, but is not limited to, injections (namely, intravenous, intramuscular and other injections as described later). The enteral administration means any form for the parenteral administration including, but is not limited to, tablet, capsules, oral solution, suspension, spray and derivatives thereof. For this purpose, the route of enteral administration means a route of transrectal and intravaginal administration. The route of topical administration means any route of administration including, but is not limited to, creams, ointments, gels and parenteral patches (also see Remington's Pharmaceutical Sciences, $18^{th}$ eds. Gennaro, et al., Mack Printing Company, Easton, Pa., 1990).

The parenteral pharmaceutical compositions of the present invention may be administered, for example, venously (intravenously), arterially (intraarterially), muscularly (intramuscularly), into the skin (subcutaneously or into depot composition), into the pericardium, by injection to coronary arteries, or with solutions for delivery to tissues or organs.

Injectable compositions may be pharmaceutical compositions that are suitable for the routes of administration by injection including, but is not limited to, injections into the veins, the arteries, the coronary vessels, into the mesothelioma, around the blood vessels, into the muscles, and subcutaneous and articular administrations. The injectable pharmaceutical compositions may be pharmaceutical compositions for direct administration into the heart, the pericardium or the coronary arteries.

For the oral administration, the pharmaceutical formulations may be ingested in a form of tablet or capsule prepared in the conventional methods, for example, with pharmaceutically available additives such as binders (for example, pregelled corn starch, polyvinyl pyrrolidone or hydroxypropyl methylcellulose); fillers (for example, lactose, microcrystalline cellulose or calcium hydrogen-phosphate); lubricants (for example, magnesium stearate, talc or silica); disintegrants (for example, potato starch or sodium starch glycolate); or wetting agents (for example, sodium lauryl sulfate). The tablets may be coated using the methods known in the art (see Remington's Pharmaceutical Sciences, $18^{th}$ eds. Gennaro et al., Mack Printing Company, Easton, Pa., 1990).

The oral pharmaceutical composition may be ingested in a form of for example, solution, syrup or suspension, or be dried products that may be mixed with water or other suitable solvents before its use. The pharmaceutical composition solution may be manufactured, using the conventional methods, with pharmaceutically available additives such as suspensions (for example, sorbitol syrup, cellulose derivatives or hydrogenated edible fats); emulsions (for example, lecithin or acacia); insoluble carriers (for example, almond oil, oil ester, ethylalcohol or fractionated vegetable oil); and preservatives (for example, methyl or propyl p-hydroxybenzoate or sorbic acid).

The pharmaceutical compositions may also include a buffer salt, a spice, a pigment and a sweetener, if necessary.

The enteral pharmaceutical compositions may be suitable for oral administration in a form of, for example, a tablet, troches or a lozenge. The peptide and/or protein of the present invention may be manufactured with solutions (rectal cream), suppositories or ointments for the routes of transrectal and intravaginal administrations. The enteral pharmaceutical compositions may be suitable for a mixed solution of a total parenteral nutrition (TPN) mixture or an intake mixture such as a solution for delivery by an intake tube (see Dudrick et al., 1998, Surg. Technol. Int. VII: 174-184; Mohandas et al., 2003, Natl Med. J. India 16 (1): 29-33; Bueno et al., 2003, Gastrointest. Endosc. 57 (4): 536-40; Shike et al., 1996, Gastrointest. Endosc. 44 (5): 536-40).

For the administration by inspiration, the peptide and/or protein of the present invention may be generally delivered in the presence of aerosol spray or in a form of a nebulizer in a container pressured with suitable propellants such as, for example, dichlorodifluoromethane, trichlorofluoromethane, dichlorotetrafluoroethane, carbon dioxide or other suitable gases. In the case of the pressured aerosol, its capacity may be determined depending on a valve for conveying its weighed amount. A capsule and, for example, a gelatine cartridge, may be formulated for use in an inhaler or an insufflator including suitable powder bases such as lactose or starch, and a powder mix of the compounds.

An eye drop of the present invention may be a soluble ophthalmic solution, an insoluble ophthalmic solution or an ophthalmic emulsion. The eye drop of the present invention may be manufactured by dissolving or suspending the peptides of the present invention in a soluble solvent such as sterilized purified water or saline, and an insoluble solvent such as vegetable oil including cotton-seed oil, soybean oil, etc. In this case, an isotonic agent, a pH modifier, thickener, a suspending agent, an emulsifying agent, a preservative, and equivalent pharmaceutically available additives may be added thereto, if necessary. More particularly, the isotonic agent includes sodium chloride, boric acid, sodium nitrate, potassium nitrate, D-mannitol, glucose, etc. A specific example of the pH modifier includes boric acid, anhydrous sodium sulfate, hydrochloric acid, citric acid, sodium citrate, acetic acid, potassium acetate, sodium carbonate, borax, etc. A specific example of the thickener includes methylcellulose, hydroxypropyl methylcellulose polyvinyl alcohol, chondroitin sodium sulfate, polyvinyl pyrrolidone, etc. A specific example of the suspending agent includes polysorbate 80, polyoxyethylene hydrogenated castor oil, etc. A specific example of the emulsifying agent includes, but is not limited to yolk lecithin, polysorbate 80, etc. A specific example of the preservative includes, but is not limited to, benzalkonium chloride, benzethonium chloride, chlorobutanol, phenylethyl alcohol, p-oxybenzoic acid ester, etc.

The composition of the present invention is administered to the subject in need of treatment of the vascular-related diseases. Toxicity and therapeutic efficiency of the composition may be determined according to the standard pharmaceutical procedure for experimental animals, such as cell culture or $LD_{50}$ (50% lethal density of one group) measurement and $ED_{50}$ (50% effective density of one group) measurement. A ratio of the added composition between the toxic effect and the therapeutic effect is referred to as a therapeutic index, and the therapeutic index may be represented by a $LD_{50}/ED_{50}$ ratio. The composition having a high therapeutic index is preferred.

In one embodiment, the data obtained from cell culture analyses and animal studies may be used to determine a dosage for application to humans. The dose of the composition according to the present invention is preferably within the range of circulating density including an $ED_{50}$ value in which the composition is not toxic or hardly toxic. The dose is varied depending on the formulations applied within the range, and the routes of administration used herein. In the composition used in the method of the present invention, a therapeutically available dose may be measured from cell culture analysis at the very beginning. The dose is designed in an animal model in order to obtain a plasma density range including an $IC_{50}$ value (namely, a density of a test material showing a half of the maximum inhibition), as determined in the cell culture. The information may be used to more correctly determine an effective dose for humans. A level of the test material in plasma may be, for example, determined by high performance liquid chromatography.

In another embodiment, an effective amount of the composition including the peptide and/or protein of the present invention may be preferably administered within a range of about 0.1 μg to about 10 mg/kg bodyweight of human patients, and more preferably about 1 to about 1000 μg/kg bodyweight of human patients. An amount of the peptide and/or protein to be administered is 0.1, 0.2, 0.5, 1, 2, 5, 10, 20, 30, 40, 50, 60, 70, 80, 90, 100, 200, 250, 300, 400, 500 or 1000 μg.

In still another embodiment, it was confirmed that an effective amount of the composition of the present invention ranges from 1 μg to 10 mg/kg bodyweight in the case of the intravenous injection, from 1 ng to 1 mg/kg bodyweight in the case of the ocular injection, and from 1 ng to 10 mg/ml of an ophthalmic suspension. The dosed composition of the present invention is preferably administered intradermally or subcutaneously. The composition may be administered on a single dose or several divided doses such as daily, every other day, weekly, every other week, or monthly dose Hereinafter, the present invention will be described.

In the present invention, it was firstly confirmed that the peptide comprising a sequence Xaa-Gly-Asp is effective for vascular diseases such as ischemia, and it might be also firstly seen that angiopoietin-1 is secreted in a process of the vascular diseases. It was confirmed that abnormal angiogenesis-related diseases may be treated using secretion of angiopoietin-1 in two cell lines and a mouse model of corneal neovascularization, and also confirmed that the polypeptide comprising a sequence Xaa-Gly-Asp has an effect to treat the abnormal angiogenesis-related diseases when it is used together with the stem cell in an intraretinal angiogenesis-induced mouse model using an oxygen partial pressure change.

Also, it was confirmed that the polypeptide comprising a sequence Xaa-Gly-Asp is effective in treating wounds of mouse skin when the wounds are treated with the polypeptide in a wound-healing mouse model, indicating that the polypeptide comprising a sequence Xaa-Gly-Asp may be useful to heal an injury and a burn and treat and prevent alopecia or trichopoliosis in normal capillary formation or obesity-associated cardiovascular diseases, as well as bedsore and chronic ulcer.

It was newly found that the polypeptide comprising a sequence Xaa-Gly-Asp induces secretion of angiopoietin-1 when the two cell lines are treated with the synthesized and purified polypeptide comprising a sequence Xaa-Gly-Asp in varying densities. It might be confirmed that this induced secretion of angiopoietin-1 helps to form normal blood vessels in the mouse model of corneal neovascularization, and reduce blood leakage in morbid angiogenic vessels having an abnormal vessel structure by stabilizing a vessel structure. Also, it might be seen that secretion of a platelet-derived growth factor (PDGF) of a normal human cell line is suppressed in platelet, wherein the platelet-derived growth factor is one of important factors for angiogenesis. Also, it was confirmed that the blood leakage and the change of vessel structure, which was observed in the abnormal angiogenesis, are suppressed, normal blood vessels are formed, and a blood vessel structure is stabilized when mononuclear cells (MNCs) comprising stem cells and the polypeptide comprising a sequence Xaa-Gly-Asp are administered together in the intraretinal angiogenesis-induced mouse model using an oxygen partial pressure change. Accordingly, the composition of the present invention is preferably used to treat retinopathy of prematurity, diabetic retinopathy, age-related macular degeneration, etc., the retinopathy of prematurity being developed as one of the ocular diseases in the normal developmental suppression, and the diabetic retinopathy and the age-related macular degeneration being ones of the abnormal angiogenesis related diseases caused by damage of the normal blood vessel structure.

BRIEF DESCRIPTION OF THE DRAWINGS

These and other features, aspects, and advantages of preferred embodiments of the present invention will be more fully described in the following detailed description, taken accompanying drawings, in the drawings.

DETAILED DESCRIPTION

Hereinafter, non-limiting preferred embodiments of the present invention will be described in detail with reference to the accompanying drawings.

Example 1

Figure 1A:
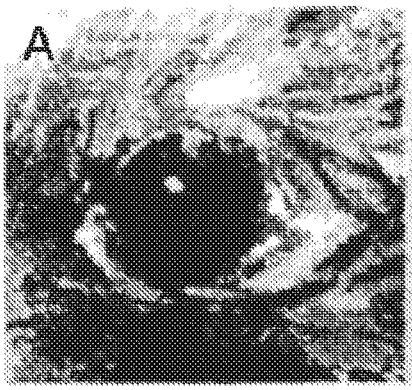
FIG. 1 is a diagram showing a procedure for forming a pocket in a mouse cornea (A and B of FIG. 1) and injecting a VEGF pellet into the pocket of the mouse cornea in an animal model (C and D of FIG. 1) were mouse corneal angiogenesis is induced by means of angiogenic factors.
Figure 1B:
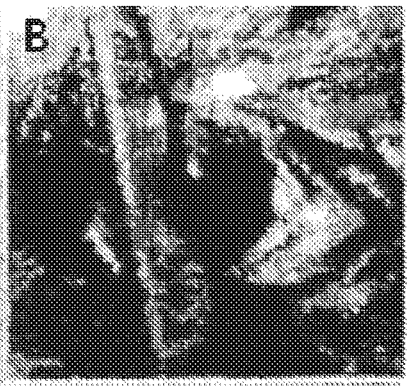
Figure 1C:
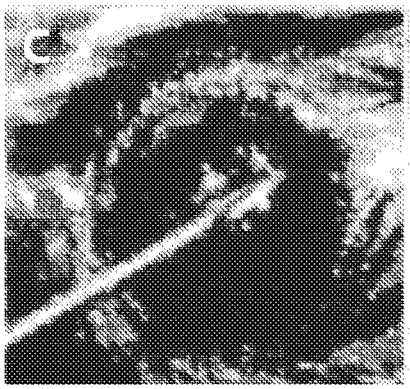
Figure 1D:
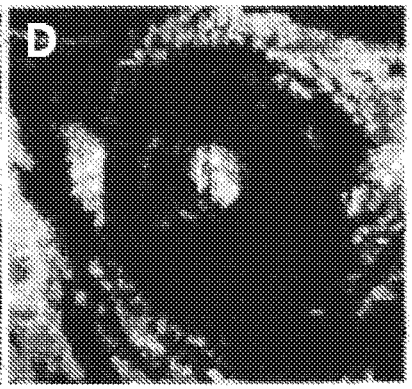
Figures 2A, 2B:
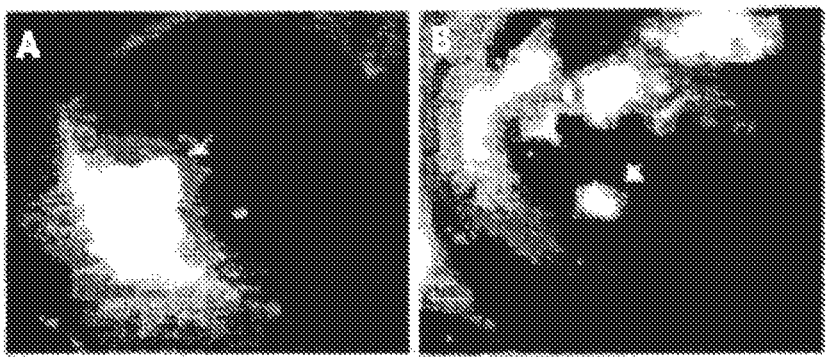
FIG. 2 is a microscopic diagram showing that normal angiogenesis is induced but abnormal angiogenesis is suppressed by the polypeptide comprising a RGD sequence when the polypeptide is administered intraperitoneally in an animal model (C and D of FIG. 2) compared to the control (A and B of FIG. 2) where mouse conical angiogenesis is induced by means of VEGF
Figures 2C, 2D:
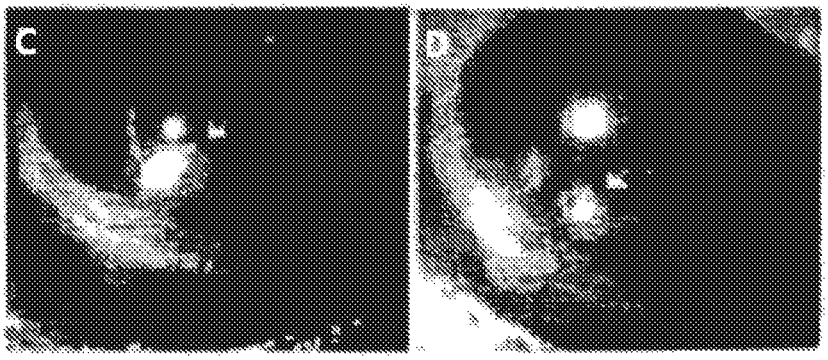
Figures 3A, 3B:
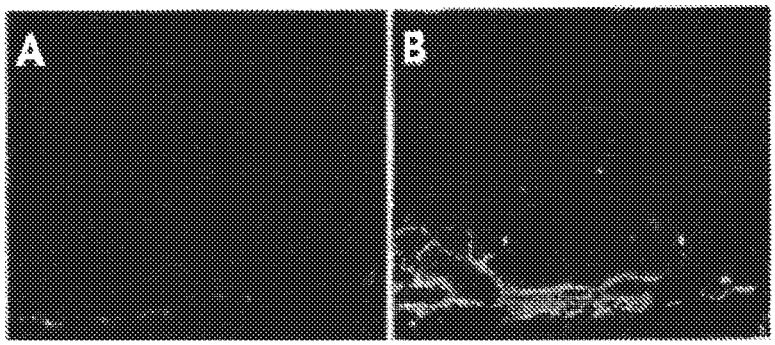
FIG. 3 is a diagram, using a fluorescent FITC-dextran, showing that normal angiogenesis is induced but abnormal angiogenesis is suppressed by the polypeptide comprising a RGD sequence when the polypeptide is administered intraperitoneally in an animal model (C and D of FIG. 3) compared to the control (A and B of FIG. 3) where mouse corneal angiogenesis is induced by means of VEGF.
Figures 3C, 3D:
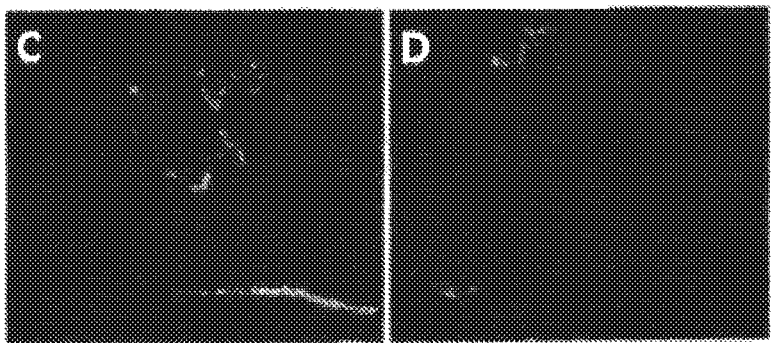
Figure 4:
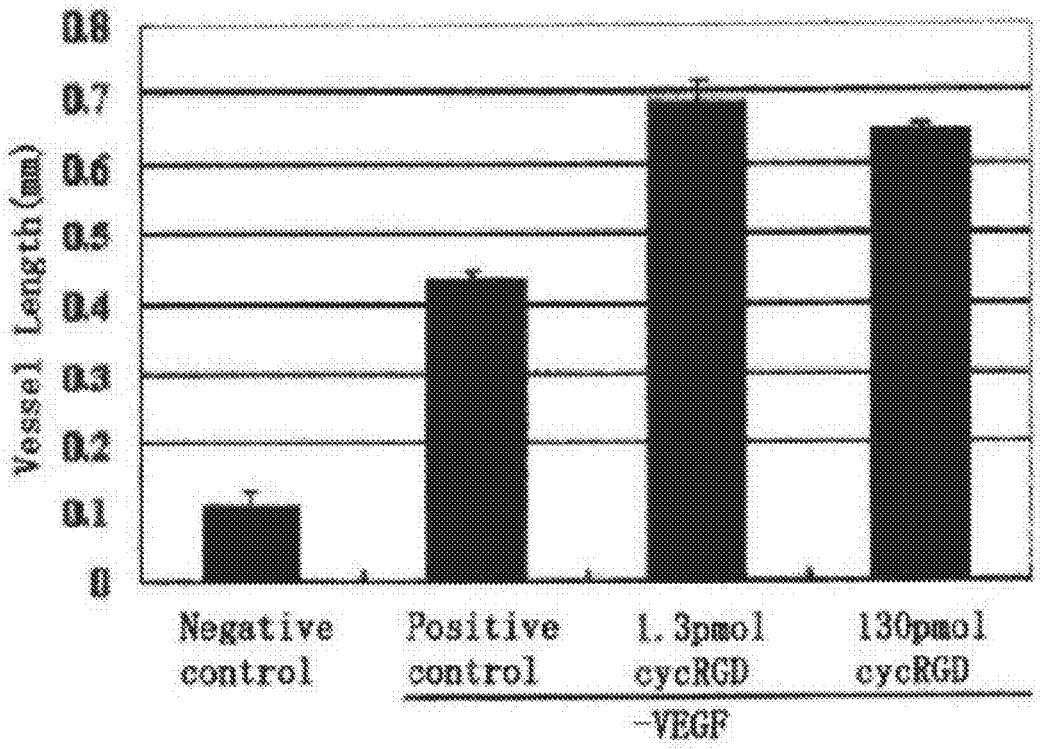
FIG. 4 is a graph showing that a production level of the angiogenesis by the polypeptide comprising a RGD sequence is digitalized when the polypeptide is administered intraperitoneally in an animal model where mouse corneal angiogenesis is induced by means of VEGF.

Effects of Treatment of RGD Sequence-Comprising Polypeptide on Quantity of VEGF-Induced Angiogenesis in Blood-Vessel-Free Ocular Corneal Tissue In order to evaluate how the polypeptide comprising a RGD sequence affects ocular angiogenesis, an animal model that a micropocket was formed in cornea of a mouse eye, and then a pellet containing 300 ng of VEGF was injected to induce angiogenesis was developed (FIG. 1). At this time, in order to determine an efficiency of the polypeptide, 1.3 pmol (0.75 ng/kg) and 130 μmol (75 ng/kg) of the polypeptide were administered intraperitoneally, respectively. 5 days after the intraperitoneal administration, the mouse eye was observed using a surgical microscope whether or not the angiogenesis is induced. As a result, it was revealed that the blood vessels were not observed in the mouse to which the VEGF-free pellet was injected (FIG. 2 and A of FIG. 3), but the angiogenesis was observed in the positive control to which the VEGF pellet was injected (FIG. 2 and B of FIG. 3). However, it was confirmed that the polypeptide comprising a RGD sequence induces proliferation of blood vessels rather than suppresses their growth since the microvascular formation and vascular networks were observed when 1.3 pmol (FIG. 2 and C of FIG. 3) and 130 pmol of the RGD sequence-comprising polypeptide were administered intraperitoneally, respectively (FIG. 2 and D of FIG. 3). When lengths of the blood vessels were measured to quantitify the angiogenesis, the total length of the blood vessels was 0.43±0.02 mm in the case of the positive control, and 0.65±0.01 mm and 0.69±0.03 mm in the case of the 1.3 pmol and 130 pmol treated groups of the cyc RGD, respectively, indicating the angiogenesis was significantly increased (FIG. 4).

Meanwhile, no side effect, such corneal opacity caused by the polypeptide comprising a RGD sequence, was observed at all in the mouse used in this experiment.

Example 2

Effects of RGD Sequence-Comprising Polypeptide (SEQ ID NOs: 1 and 2) in Mouse Model for Inducing Retinal Angiogenesis Using Oxygen Partial Pressure The artificial ocular angiogenesis by oxygen partial pressure difference exhibited the same pattern as in human retinopathy of prematurity and diabetic retinopathy. This experiment was carried out using a principle that abnormal angiogenesis is spontaneously induced when a mouse is subject to a high oxygen environment (75%) at an early stage of its birth, and then returned to a normal oxygen partial pressure (Higgins R D. et al., Curr Eye Res. 18:20-27 (1999); Bhart N. et al., Pediatric Res. 46:184-188 (1999); Gebarowska D. et al., Am. J. Pathol. 160:307-313 (2002)). For this purpose, a mouse was kept for 5 days under a high oxygen environment with a constant 75% oxygen partial pressure 7 days after the mouse was born in an apparatus that can adjust an oxygen partial pressure, and then kept under a 20% oxygen pressure which is a normal oxygen partial pressure. At this time, the peptide (SEQ ID NO: 1 or SEQ ID NO: 2) comprising a RGD sequence was administered intraperitoneally once every five days to observe whether or not the angiogenesis was induced in the mouse eye. In order to observe the blood vessels, 50 mg of FITC-dextran having a molecular weight of $2\times10^6$ was dissolved in 1 ml of saline, and the resultant solution was injected through the left ventricle. The mouse eyeball was extracted immediately after the injection. The extracted eyeball was washed with saline, fixed with 4% paraformaldehyde for 4 to 24 hours, and then a lens was removed from the eyeball. Then, the resultant mouse retina was evenly spread over a glass slide, and the glass slide was sealed with glycerine-gelatin, and then observed using a fluorescence microscope.

Figure 5A:
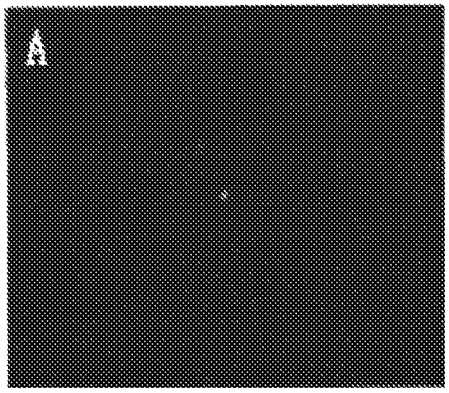
FIG. 5 is a diagram showing comparison of a retina (A of FIG. 5) whose mouse does not exhibit a normal angiogenesis and a retina (B of FIG. 5) whose mouse normally grows in a normal oxygen partial pressure when the mouse retina is exposed to a high oxygen pressure in an animal model where mouse retinal angiogenesis is induced by lowering the high oxygen pressure to a normal oxygen partial pressure after the high-pressure oxygen treatment (75%).
Figure 5B:
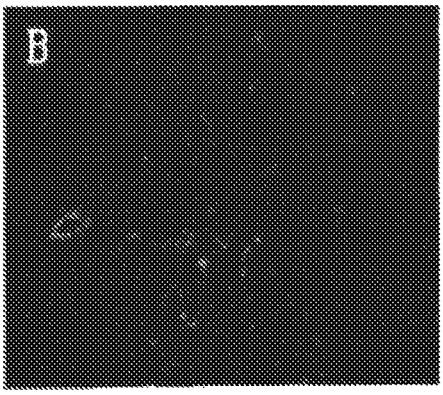
Figure 6A:
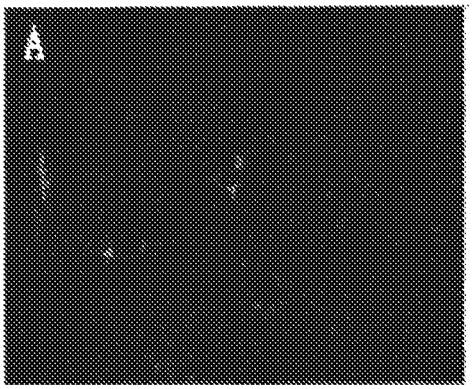
FIG. 6 is a diagram, using a fluorescent FITC-dextran, showing that normal angiogenesis is not induced by the polypeptide comprising a sequence RAD (SEQ. ID NO: 3) (A of FIG. 6), while normal angiogenesis is induced and blood leakage is reduced by the polypeptide comprising a sequence RGD (SEQ ID NOs: 1 and 2) (B and C of FIG. 6) when the polypeptide is administered intraperitoneally in an animal model where mouse retinal angiogenesis is induced by lowering the high oxygen pressure to a normal oxygen partial pressure after the high-pressure oxygen treatment (75%).
Figure 6B:
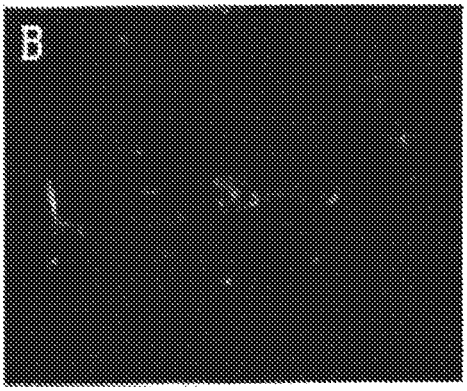

It was observed that the blood vessels was uniformly distributed over the entire retina of the mouse that grown in a normal oxygen partial pressure (B of FIG. 5), and the most angiogenesis was abnormal and the ischemia was developed in the mouse that was treated with the high-pressure oxygen and then the saline (A of FIG. 5). Also, it was observed that a blood vessel tissue was not normally formed during a development stage in the retina of the mouse treated with the high-pressure oxygen, compared to the normal mouse, and the retinal blood vessels was not also normally formed when the mouse was treated with the polypeptide comprising a RAD sequence as the control (A of FIG. 6). However, it was revealed that the abnormal angiogenesis was not observed in the mouse treated daily with 1 μg/kg of the polypeptide comprising a RGD sequence (B and C of FIG. 6), and the normal blood vessels were observed without any abnormal angiogenesis. This is a very interesting result in that the polypeptide comprising a RGD sequence functions to help growth of normal blood vessels, indicating that the polypeptide may be used for treating the ocular diseases such as retinopathy of prematurity since the polypeptide comprising a RGD sequence suppresses a morbid angiogenesis by reducing an oxygen-deficit region, thereby removing underlying causes of the angiogenesis in the mouse model for inducing a retinal angiogenesis using the oxygen partial pressure change. Also, it was observed from the leakage test using a fluorescent FITC-dextran that blood was not leaked since the a blood vessel structure was stabilized by means of the treatment with the polypeptide comprising a RGD sequence. Regions in which the fluorescent leaks out and spreads in the FITC photograph represents, for example, regions that the blood was leaked through punctures of the blood vessels. As a result, it was understood that the fact that the spreading of the fluorescent is reduced by the peptide of the present invention means that damages of the blood vessels were prevented as much as the reduced spreading of the fluorescent.

Since blood-retina-barriers (BRBs) such as cerebrovascular blood-brain-barriers (BBBs) are present in retinal blood vessels, large molecules are not easily passed through the retinal blood vessels. It was experimentally proven that the fact that higher molecules such as FITC-dextran are leaked into the retina means that microstructures of the retinal blood vessels are greatly damaged, and the secretion of the angiopoietins by the polypeptide comprising a RGD sequence prevents the damage of the retinal blood vessels. Accordingly, the polypeptide comprising a RGD sequence may be used as a therapeutic agent for treating diseases such as diabetic retinopathy and age-related macular degeneration since the polypeptide may maintain a vessel structure in early stages of the diseases (the angiogenesis was not induced in the early stages of the diseases) even if the diseases are developed due to the blood leakage in the blood vessels.

Example 3

Figure 7A:
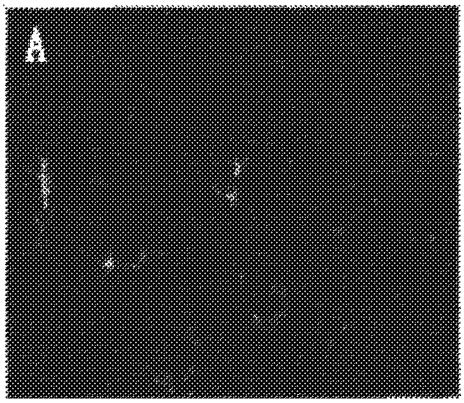
FIG. 7 is a diagram, using a fluorescent FITC-dextran, showing that normal angiogenesis is induced and blood leakage is reduced by the polypeptide (SEQ. ID NOs: 6 and 7) comprising a sequence RGD (A and B of FIG. 7) when the polypeptide is administered intraperitoneally in an animal model where mouse retinal angiogenesis is induced by lowering the high oxygen pressure to a normal oxygen partial pressure after the high-pressure oxygen treatment (75%).
Figure 7B:
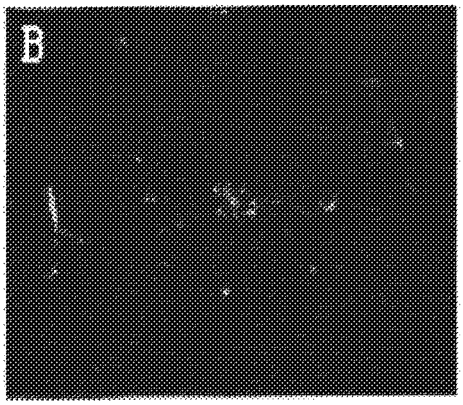

Effects of RGD Sequence-Comprising Polypeptide (SEQ ID NOs: 6 and 7) in Mouse Model for Inducing Retinal Angiogenesis Using Oxygen Partial Pressure In Example 3, an effect of the polypeptide (SEQ ID NOs: 6 and 7) comprising a RGD sequence was confirmed in a mouse model for inducing an artificial retinal angiogenesis using oxygen partial pressure, as described in Example 2. It was confirmed that the blood vessels are uniformly distributed over the entire retina in the mouse that grows in a normal oxygen partial pressure as described in Example 6 (B of FIG. 5), and the most angiogenesis was abnormal and the ischemia was developed in the mouse that was treated with the high-pressure oxygen and then the saline (A of FIG. 5). It was revealed that the abnormal angiogenesis was not observed in the mouse treated daily with 1 μg/kg of the polypeptide comprising a RGD sequence (A and B of FIG. 7), and the normal blood vessels were observed without any abnormal angiogenesis. This means that the polypeptide comprising a RGD sequence functions to help growth of normal blood vessels, as described in Example 2. The polypeptide (SEQ ID NOs: 6 and 7) comprising a RGD sequence may be used as a therapeutic agent for treating diseases such as diabetic retinopathy and age-related macular degeneration since the polypeptide may maintain a vessel structure in early stages of the diseases (the angiogenesis was not induced in the early stages of the diseases) even if the diseases are developed due to the blood leakage in the blood vessels.

Example 4

Figure 8:
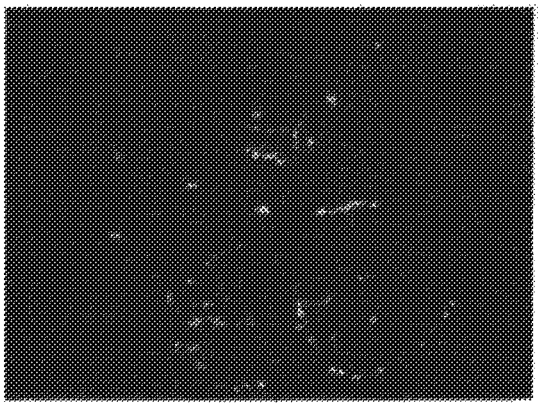
FIG. 8 is a diagram, using a fluorescent FITC-dextran, showing that normal angiogenesis is induced and blood leakage is reduced b the polypeptide (SEQ ID NO: 8) comprising a sequence RGD when the polypeptide is administered intraperitoneally in an animal model where mouse retinal angiogenesis is induced by lowering the high oxygen pressure to a normal oxygen partial pressure after the high-pressure oxygen treatment (75%).

Effects of RGD Sequence-Comprising Polypeptide (SEQ ID NO: 8) in Mouse Model for Inducing Retinal Angiogenesis Using Oxygen Partial Pressure In Example 4, an effect of the polypeptide (SEQ ID NO: 8) comprising a RGD sequence was confirmed in a mouse model for inducing an artificial retinal angiogenesis using oxygen partial pressure, as described in Example 2. It was revealed that the abnormal angiogenesis was not observed in the mouse treated daily with 1 μg/kg of the polypeptide comprising a RGD sequence, and the normal blood vessels were observed without any abnormal angiogenesis (FIG. 8). This means that the polypeptide comprising a RGD sequence functions to help growth of normal blood vessels, as described in Example 2. The polypeptide comprising a RGD sequence may be used as a therapeutic agent for treating diseases such as diabetic retinopathy and age-related macular degeneration since the polypeptide may maintain a vessel structure in early stages of the diseases (the angiogenesis was not induced in the early stages of the diseases) even if the diseases are developed due to the blood leakage in the blood vessels.

Example 5

Figure 9A:
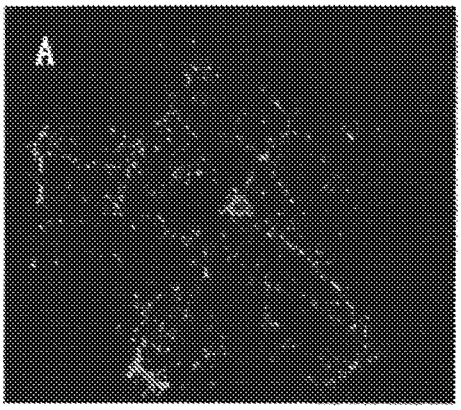
FIG. 9 is a diagram, using a fluorescent FITC-dextran, showing that normal angiogenesis is induced and blood leakage is reduced by echistatin (A of FIG. 9) and kistrin (B of FIG. 9) when the echistatin and the kistrin are administered intraperitoneally in an animal model where mouse retinal angiogenesis is induced by lowering the high oxygen pressure to a normal oxygen partial pressure after the high-pressure oxygen treatment (75%).
Figure 9B:
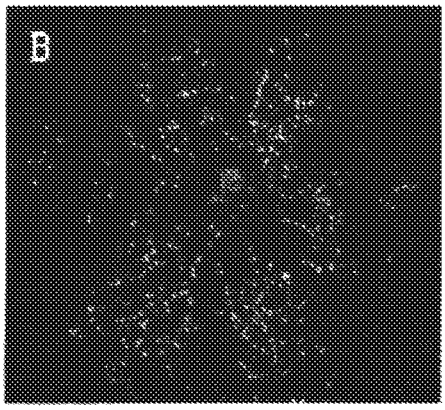
Figure 10A:
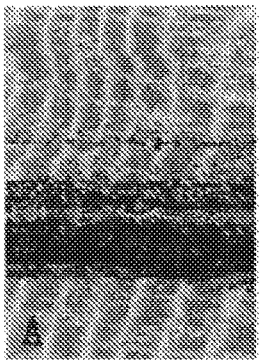
FIG. 10 is a diagram of H&E-stained tissues showing that an inner ganglion cell layer maintains a normal thickness without any hypertrophy (C and D of FIG. 10) at a similar level to the normal mouse (A of FIG. 10) by the polypeptide (SEQ ID NOs: 6 and 8) comprising a sequence RGD, compared to that of the negative control (B of FIG. 10), when the polypeptide is administered intraperitoneally in an animal model where mouse retinal angiogenesis is induced by lowering the high oxygen pressure to a normal oxygen partial pressure after the high-pressure oxygen treatment (75%).
Figure 10B:
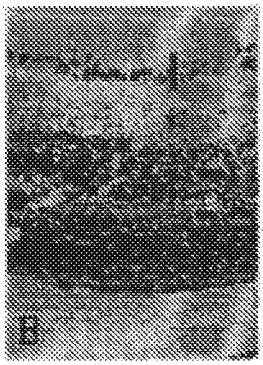
Figure 10C:
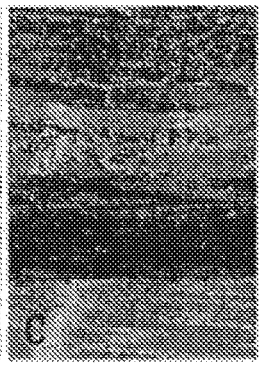
Figure 10D:
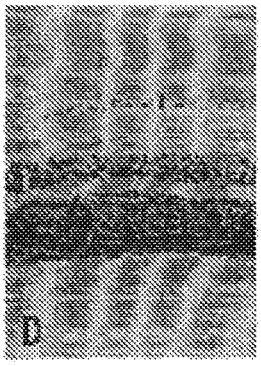

Effects of Echistatin (SEQ ID NO: 9) and Kistrin (SEQ ID NO: 10) in Mouse Model for Inducing Retinal Angiogenesis Using Oxygen Partial Pressure In Example 5, effects of the echistatin and the kistrin, which are polypeptides comprising a RGD sequence, were confirmed in a mouse model for inducing an artificial retinal angiogenesis using oxygen partial pressure, as described in Example 2. It was confirmed that the blood vessels are uniformly distributed over the entire retina in the mouse that grows in a normal oxygen partial pressure as described in Example 2 (B of FIG. 5), and the most angiogenesis was abnormal and the ischemia was developed in the mouse that was treated with the high-pressure oxygen and then the saline (A of FIG. 5). It was revealed that the abnormal angiogenesis was not observed in the mouse treated daily with 1 μg/kg of the echistatin and the kistrin (FIG. 9), and the normal blood vessels were observed without any abnormal angiogenesis. This means that the polypeptide comprising a RGD sequence functions to help growth of normal blood vessels, as described in Example 2.

Example 6

Effects of RGD Sequence-Comprising Polypeptide (SEQ ID NOs: 6 and 8) in Histological Photograph of Mouse Model for Inducing Retinal Angiogenesis Using Oxygen Partial Pressure In Example 6, effects of the polypeptide (SEQ ID NOs: 6 and 8) comprising a RGD sequence, were confirmed using histological staining in a mouse model for inducing an artificial retinal angiogenesis using oxygen partial pressure, as described in Example 2. A C57BL/6 mouse was kept for 5 days under a high oxygen environment with a constant 75% oxygen partial pressure 7 days after the mouse was born in an apparatus that can adjust an oxygen partial pressure, and then kept for 5 days under a 20% oxygen pressure which is a normal oxygen partial pressure, as described in Example 2. At this time, the polypeptide (SEQ ID NO: 6 or SEQ ID NO: 8) comprising a RGD sequence was administered intraperitoneally once every five days, respectively, and then the retina was extracted from the C57BL/6 mouse, fixed with paraffin, cut into 6-um paraffin cross-sections, histologically stained with an H&E stain, and then the stained paraffin cross-sections was observed using a microscope. It was shown that an inner ganglion cell layer of the retina maintains a normal cell thickness without any hypertrophy in the normal mouse (A of FIG. 10), and the inner ganglion cell layer of the retina was abnormally hypertrophied by the oxygen partial pressure difference in the negative control (B of FIG. 10). It was shown that the mouse treated with the polypeptide (SEQ ID NOs: 6 and 8) comprising a sequence RGD maintains the inner ganglion cell layer to a normal thickness without any hypertrophy at the same level as in the normal mouse, compared to that of the negative control (C and D of FIG. 10). This means that the polypeptide comprising a RGD sequence functions to help growth of normal blood vessels, as described in Examples 3 and 4, as well as maintains the retina at a normal level by maintaining the inner ganglion cell layer to a normal thickness without any hypertrophy. As another result, it was shown that the polypeptide (SEQ ID NOs: 6 and 8) comprising a RGD sequence may be used as a therapeutic agent for treating diseases such as diabetic retinopathy and age-related macular degeneration since the polypeptide may maintain a vessel structure in early stages of the diseases (the angiogenesis was not induced in the early stages of the diseases) even if the diseases are developed due to the blood leakage in the blood vessels.

Example 7

Figure 11A:
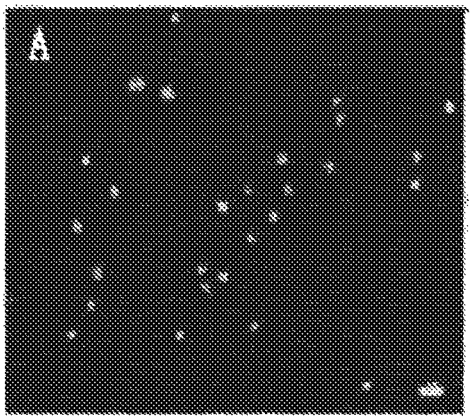
FIG. 11 is a microscopic diagram showing that the whole mononuclear cells (MNCs) are separated from a mouse hone marrow, and then stained with fluorescents Hoechst-33342 (A of FIG. 11) and FITC (B of FIG. 11), respectively.
Figure 11B:
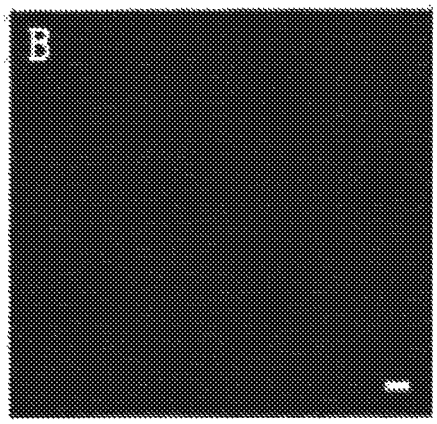

Effects of RGD Sequence-Comprising Polypeptide and Mononuclear Cell (MNC) in Mouse Model for Inducing Retinal Angiogenesis Using Oxygen Partial Pressure Preparation of Mononuclear Cell Group In order to separate a mononuclear cell group, the thighbones and the shinbones were separated from both legs of a C57BL/6 mouse and put into a DMEM medium containing 50 unit of heparin. In order to obtain bone marrow cells from the separated thighbones and shinbones, the heads and the epiphyses of the separated bones was cut to expose medullary cavities, and 10 ml of DMEM medium was injected into the exposed medullary cavities using a needle 22G to separate bone marrow cells. In order to separate fats and muscle tissues from the separated bone marrow cells, a bone marrow cell suspension was filtered using a 70 um nylon mesh cell strainer. Ficoll-Paque Plus (a density of 1.077 mg/ml) was added 1.5 times as much as the bone marrow cell suspension, and centrifuged at 3,000 rpm for 20 minutes at a room temperature to separate a mononuclear cell group which is present in an interfacial region between the Ficoll-Paque and the medium. The separated mononuclear cell group was washed twice with a DMEM medium, and then suspended in 1 ml of a DMEM medium containing 2% fetal bovine serum and 1 mM HEPES. The separated mononuclear cell group has a density of $1.1\sim3.2\times10^6$ cells/mouse, and the mononuclear cells were stained using Hoechst 33342, and then observed (A of FIG. 11).

Test of Inducing Retinal Angiogenesis

In Example 7, effects of the mononuclear cell group and/or the polypeptide (SEQ ID NO: 5) comprising a RGD sequence, were confirmed at a postnatal day 20 (PN20) and a postnatal day 27 (PN27) under the conditions as listed in following Table 1, by using a mouse model for inducing an artificial retinal angiogenesis using oxygen partial pressure, as described in Example 2.

TABLE 1

Cell Number of Mononuclear Cells used in Test for Inducing Retinal Angiogenesis

| | | Mean Cell Number ($\times10^6$ cells) | Standard Deviation | P value |
|---|---|---|---|---|
| 1 | MNC (PN20) | 1.4 | 0.53 | |
| 2 | Polypeptide (PN20) with MNC + RGD Sequence | 1.1 | 0.70 | 0.089 |
| 3 | Polypeptide (PN27) with RGD Sequence | — | — | — |
| 4 | MNC (PN27) | 3.2 | 0.86 | |
| 5 | Polypeptide (PN27) with MNC + RGD Sequence | 1.8 | 0.70 | 0.009 |
| | Mean Cell Number ($\times10^6$ cells) | 1.9 | | |

Figure 12A:
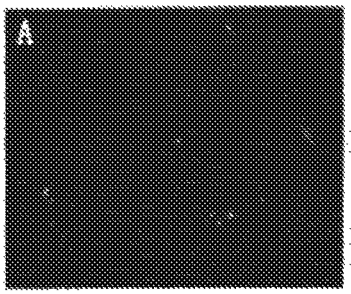
FIG. 12 is a diagram, using a fluorescent FITC-dextran, showing that a mouse retina is separated and observed at a postnatal day 20 after the polypeptide (SEQ ID NO: 5) comprising a RGD sequence and the mononuclear cells (MNCs) are administered intraperitoneally alone (A and B of FIG. 12, respectively) or in combination thereof (C of FIG. 12) in an animal model where mouse retinal angiogenesis is induced by lowering the high oxygen pressure to a normal oxygen partial pressure after the high-pressure oxygen treatment (75%), wherein normal angiogenesis is more induced and blood leakage is more reduced when the mononuclear cells is administered intraperitoneally alone than when it is administered intraperitoneally in combination with the polypeptide comprising a RGD sequence.
Figure 12B:
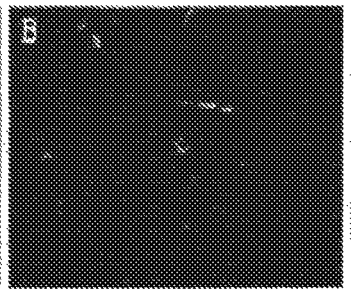
Figure 12C:
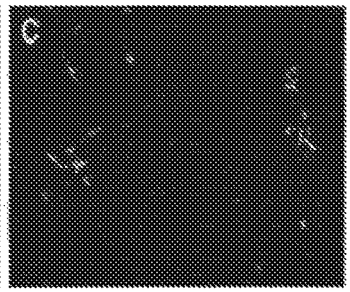
Figure 13A:
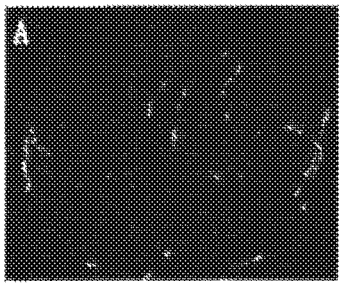
FIG. 13 is a diagram, using a fluorescent FITC-dextran, showing that a mouse retina is separated and observed at a postnatal day 27 after the polypeptide (SEQ ID NO: 5) comprising a RGD sequence and the mononuclear cells (MNCs) are administered intraperitoneally alone (A and B of FIG. 13, respectively) or in combination thereof (C of FIG. 13) in an animal model where mouse retinal angiogenesis is induced by lowering the high oxygen pressure to a normal oxygen partial pressure after the high-pressure oxygen treatment (75%), wherein normal angiogenesis is more induced and blood leakage is more reduced when the mononuclear cells is administered intraperitoneally alone than when it is administered intraperitoneally in combination with the polypeptide comprising a RGD sequence.
Figure 13B:
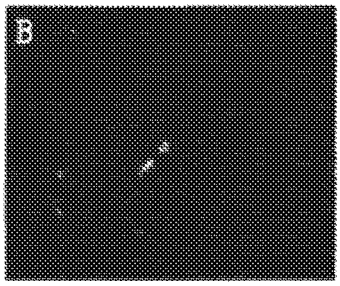
Figure 13C:
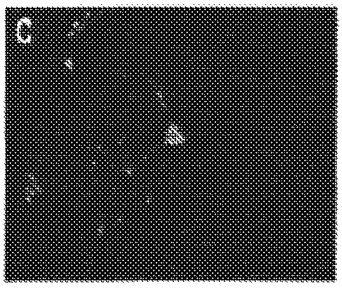

As listed in Table 1, it was revealed that the abnormal angiogenesis was not observed but the normal blood vessels were observed without any abnormal 15 angiogenesis at both the postnatal day 20 (PN20) and the postnatal day 27 (PN27) in the mouse (FIG. 12, B of FIG. 13) treated with the mononuclear cell group and the polypeptide comprising a RGD sequence together, compared to the mouse (FIG. 12, C of FIG. 13) treated alone with the mononuclear cell group or the polypeptide comprising a RGD sequence. As a result, it was seen that, if the stem cell was used along with the polypeptide comprising a RGD sequence, the resultant mixture may be used as a therapeutic agent for treating diseases such as diabetic retinopathy and age-related macular degeneration since the polypeptide may maintain a vessel structure in early stages of the diseases (the angiogenesis was not induced in the early stages of the diseases) even if the diseases are developed due to the blood leakage in the blood vessels.

Example 8

Effects of RGD Sequence-Comprising Polypeptide on Healing Wounds Using a Mouse

Figure 14:
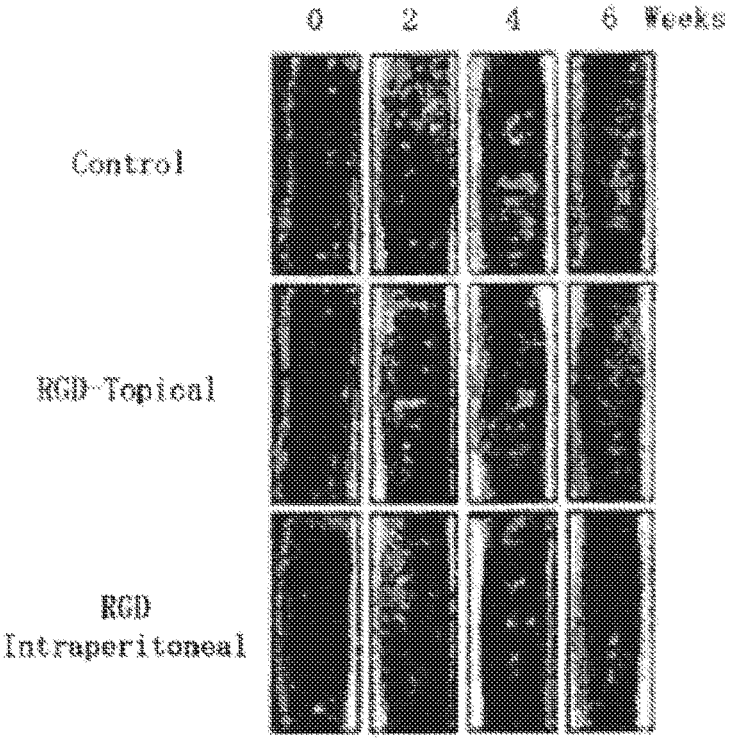
FIG. 14 is a diagram showing that an injury of mouse skin is more significantly reduced than that of the control when the injury is treated with the polypeptide comprising a RGD sequence in a wound-healing mouse model.
Figure 15:
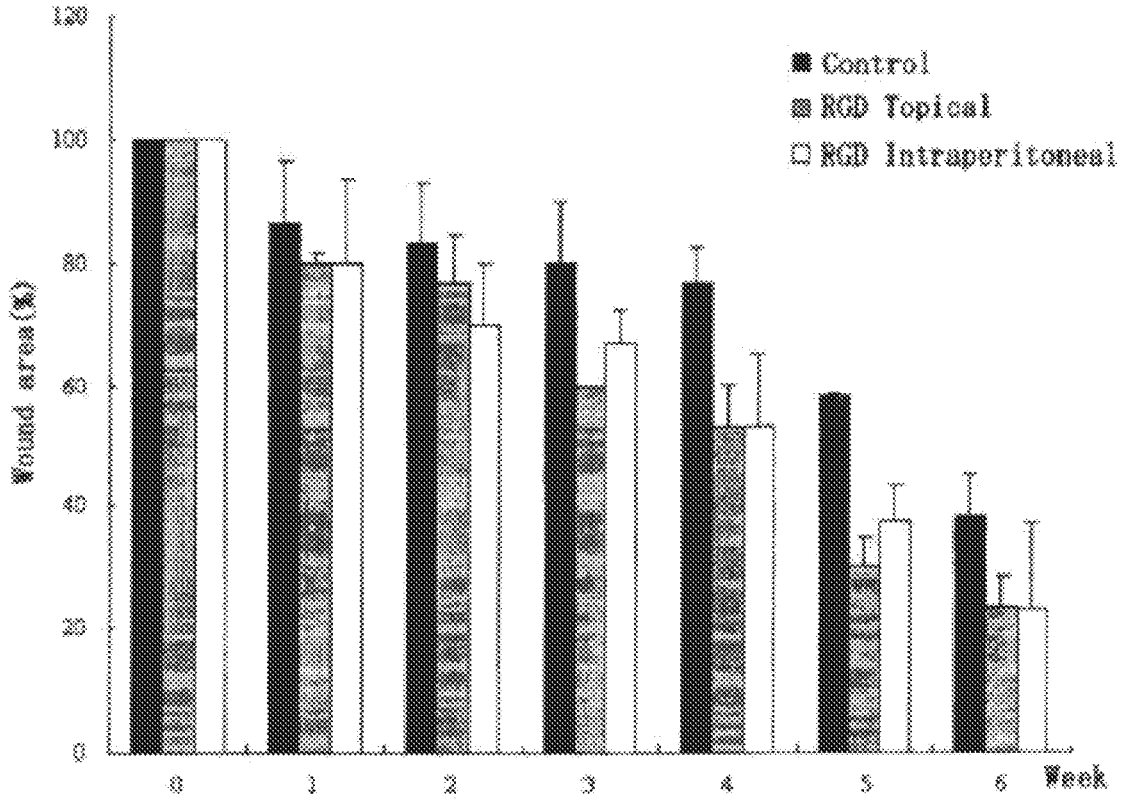
FIG. 15 is a schematic graph showing that an injury of mouse skin is more significantly reduced than that of the control when the injury is treated with the polypeptide comprising a RGD sequence in a wound-healing mouse model.
Figure 16A:
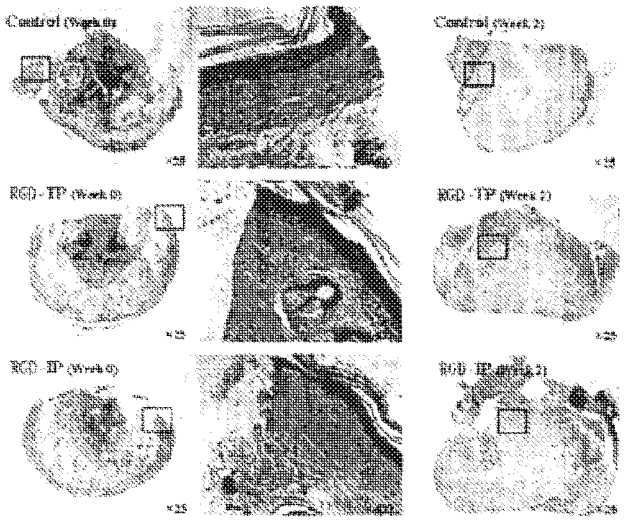
FIG. 16 is a diagram of H&E-stained tissues showing that fine capillary vessels formed beneath the injured skin tissue grow into thick blood vessels as shown in a normal mouse, compared to the control, when the injury is treated with the polypeptide comprising a RGD sequence in a wound-healing mouse model.
Figure 16B:
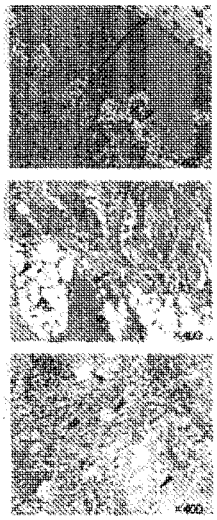
Figure 16C:
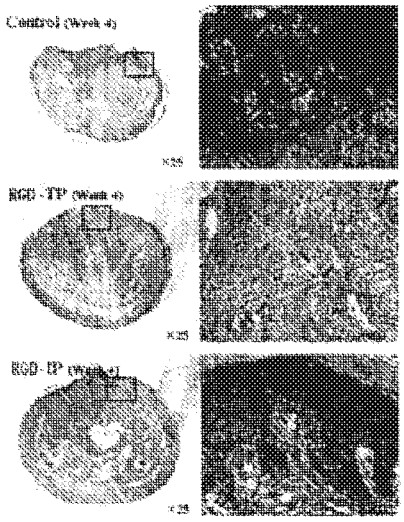

In order to examine effects of the polypeptide comprising a RGD sequence on healing wounds, an excisional full-thickness wound of 10×3 mm was made in the dorsal side of the tail which is about 0.5-1.0 cm from the mouse body (FIG. 14). Bleeding was stopped with pressure in inflicting an injury, and infection of the wound was prevented using a spray coating method. Meanwhile, in order to confirm an efficacy of the polypeptide, the polypeptide was administered once daily for 4 weeks in a concentration of 1 μg/kg via two route of administration. One route of administration is to directly drop a polypeptide-containing solution over an injury, and the other route of administration is to inject a polypeptide-containing solution intraperitoneally. In order to confirm the experimental results, a size of the injury inflicted in the mouse tail was measured every week, and tissue samples of the mouse tail was taken once every two week, embedded in a paraffin block, and then stained with HE stain to observe a histological change. As a result, it was confirmed from the photograph that the injury of the mouse into which the polypeptide is administered is significantly reduced 3 weeks after the intraperitoneal administration regardless of the routes of administration, compared to the control (FIG. 14), and then the reduction in the injury of the mouse was digitized and illustrated as a graph (FIG. 15). Also, in the observation of the histological change through the HE staining, thick blood vessels were observed in large numbers in the tissue of the mouse into which the polypeptide was administered 2 weeks after the administration (FIG. 16), contrary to the control in which fine capillary vessels were observed in small numbers in the tissue beneath the scar. It was anticipated that the RGD sequence-comprising polypeptide may have an effect to treat alopecia or trichopoliosis or treat and prevent diseases such as obesity-associated arteriosclerosis and myocardial infarction by stabilizing the blood vessel formation to normally form hair follicles, as well as to heal an injury or a burn and treat and prevent diseases such as bedsore and chronic ulcer.

Example 9

Secretion of Angiopoietin-1 in Fibrosarcoma Cell Line by RGD Sequence-Comprising Polypeptide Fibrosarcoma Cell Culture Fibrosarcoma cell (Human) was incubated at 37° C. in a 10% FBS-supplemented MEM in a 5% $CO_2$ incubator. The fibrosarcoma cell grown to at least 90% confluence in a dish was used herein.

Measurement of Secreted Angiopoietin-1

Figure 17:
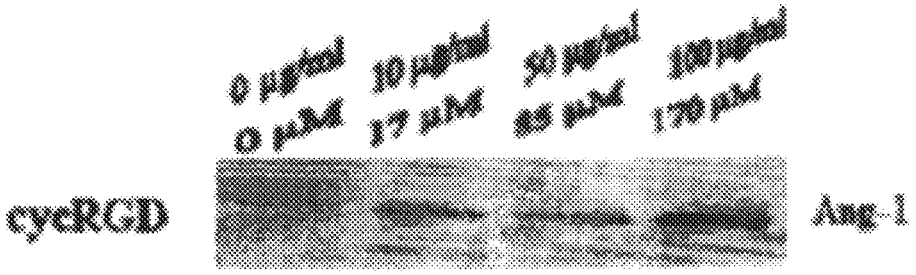
FIG. 17 is a diagram showing that angiopoietin-1 is secreted in a sarcoma cell treated with the polypeptide comprising a. RGD sequence.

The fibrosarcoma cell, which was grown in a 6-well plate to a density of $2\times10^5$, was treated with 0-100 μg/ml of the polypeptide comprising a RGD sequence. After the treatment, secretion of angiopoietin-1 was induced for 12 hours. At this time, the quantity of the secreted angiopoietin-1 was measured using a western blotting method (FIG. 17).

Example 10

Secretion of Angiopoietin-1 in Mouse Plasma by RGD Sequence-Comprising Polypeptide (SEQ ID NO: 5)

Figure 18:
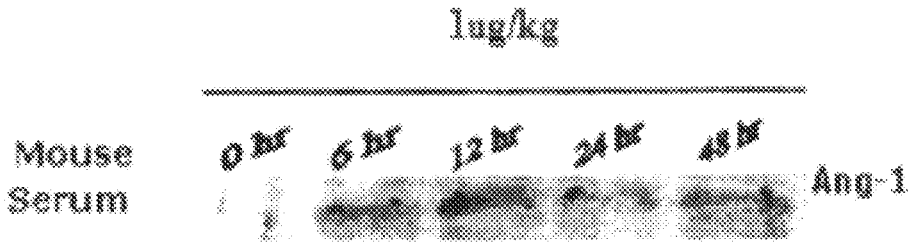
FIG. 18 is a diagram showing that angiopoietin-1 is secreted in mouse plasma treated with the polypeptide comprising a RGD sequence.

In order to determine secretion of angiopoietin-1 in mouse plasma by the polypeptide comprising a RGD sequence, this experiment was carried out using a principle that abnormal angiogenesis is spontaneously induced when a mouse is subject to a high oxygen environment (75%) at an early stage of its birth, and then returned to a normal oxygen partial pressure (Higgins R D. et al., Curr. Eye Res. 18:20-27 (1999); Bhart N. et al., Pediatric Res. 46:184-188 (1999); Gebarowska D. et al., Am. J. Pathol. 160:307-313 (2002)). For this purpose, a mouse was kept for 5 days under a high oxygen environment with a constant 75% oxygen partial pressure 7 days after the mouse was born in an apparatus that can adjust an oxygen partial pressure, and then kept under a 20% oxygen pressure which is a normal oxygen partial pressure. At this time, 1 μg/kg of the polypeptide comprising a RGD sequence was administered intraperitoneally to induce secretion of angiopoietin-1. Then, the plasma was separated at predetermined time points, and then the quantity of the angiopoietin-1 was measured using a western blotting method (FIG. 18).

Example 11

Secretion of Angiopoietin-1 in Fibrosarcoma Cell Line by KGD Sequence-Comprising Polypeptide (SEQ ID NO: 4)

Fibrosarcoma Cell Culture

Fibrosarcoma cell (Human) was incubated at 37° C. in a 10% FBS-supplemented MEM in a 5% $CO_2$ incubator. The fibrosarcoma cell, which was grown to at least 90% confluence in a dish, was used herein.

Measurement of Secreted Angiopoietin-1

Figure 19:
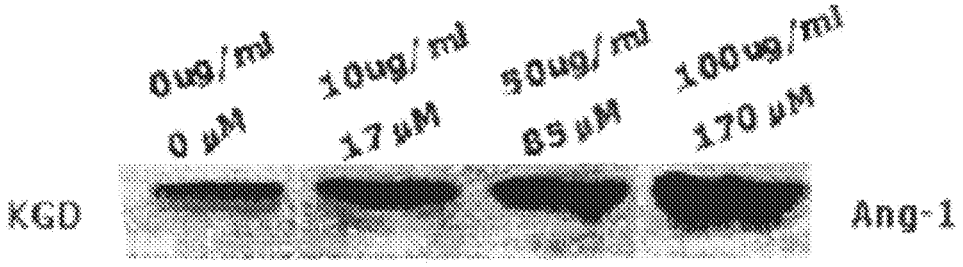
FIG. 19 is a diagram showing that angiopoietin.-1 is secreted in a sarcoma cell line treated with the polypeptide comprising a KGD sequence.

The fibrosarcoma cell, which was grown in a 6-well plate to a density of $2\times10^5$, was treated with 0-100 μg/ml of the polypeptide comprising a KGD sequence. After the treatment, secretion of angiopoietin-1 was induced for 12 hours. At this time, the quantity of the secreted angiopoietin-1 was measured using a western blotting method (FIG. 19).

Example 12

Effect of RGD Sequence-Comprising Polypeptide on Suppression of PDGF (Platelet Derived Growth Factor) Expression in Platelet Preparation of Platelet Whole blood was extracted from a healthy donor in a vacuatainer containing 3.8% sodium citrate as an anticoagulant, and then centrifuged at 1,200 rpm to separate platelet-rich plasma (PRP). The platelet-rich plasma (PRP) was centrifuged at 1,200 rpm in the presence of 1 mM prostaglandin E1 to obtain a pellet of platelet. The pellet of platelet was re-suspended in a modified Tyrode's-HEPES buffer (140 mM sodium chloride, 2.9 mM potassium chloride, 1 mM magnesium chloride, 5 mM glucose, 10 mM HEPES, pH 7.4).

Activation of Platelet by Collagen

Figure 20:
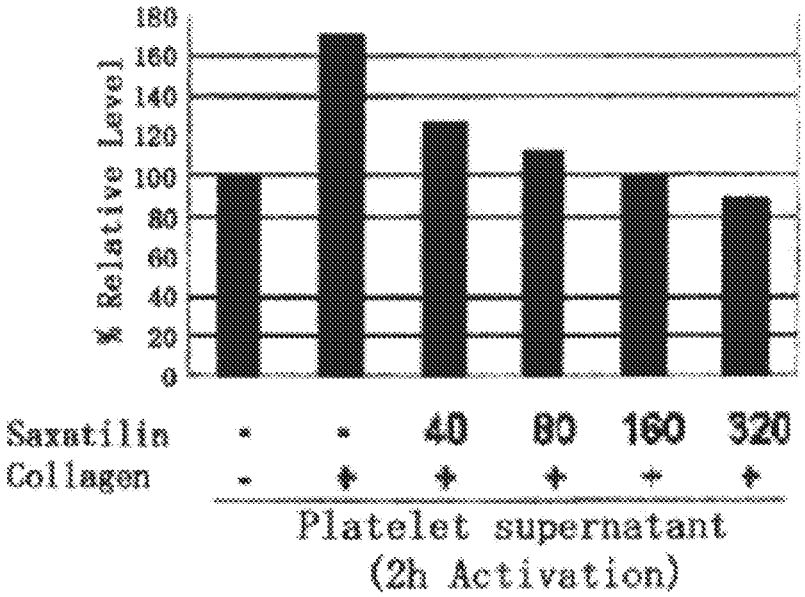
FIG. 20 is a graph showing that production of a platelet-derived growth factor (PDGF) is suppressed in platelet by the polypeptide (SEQ ID NO: 5) comprising a RGD sequence.

The platelet suspension ($2\times10^8$/ml), which was washed once, was pre-treated with and/or without the polypeptide (SEQ ID NO: 5) comprising a RGD sequence for 10 minutes at a room temperature, and then activated by treating the platelet suspension with collagen (2 μg/ml). After the platelet suspension was activated for 2 hours at a room temperature, it was centrifuged at 1,500 rpm for 5 minutes at 4° C. The resultant supernatant was collected, and then the secreted platelet derived growth factor (PDGF) was quantified using an EIA method. As a result, it was confirmed that an amount of the secreted platelet derived growth factor (PDGF) was significantly reduced by the treatment of the polypeptide (FIG. 20).

In recent years, it has been reported that angiopoietin-1 is secreted in platelet, which is one of many evidences that the activation of platelet takes an important role in the angiogenesis. The suppression of the PDGF secretion by the polypeptide comprising a RGD sequence may be described in connection with an intrinsic function of disintegrin that prevents platelet coagulation to suppress the angiogenesis, and it was also considered that the angiopoietin-1 is secreted to induce normal angiogenesis since the polypeptide suppresses interaction among the platelets due to the platelet coagulation when the platelet was treated with a low density of the polypeptide comprising a RGD sequence.

According to the present invention, there is proposed the novel therapeutic method using a therapeutic agent in addition to the method for treating angiogenesis-related ocular diseases, which mainly depends on conventional surgical operations. The surgical operations are very expensive and difficult to be applied to all patients, but the method of the present invention is very epochal in treating the angiogenesis-related ocular diseases, as well as preventing loss of eyesight. The secretion of the angiopoietin-1 by the polypeptide comprising a specific amino acid sequence of the present invention does not affect the existing normal blood vessels and normal blood vessels that are newly formed in a development stage. On the contrary, the secretion of the angiopoietin-1 is very effective for patients with incipient retinopathy of prematurity since the secretion of the angiopoietin-1 aids to form normal blood vessels in a development stage. Also, it was known that the stem cells rather than the hematopoietic stem cells functions together with the polypeptide comprising an Xaa-Gly-Asp sequence to form normal blood vessels. The polypeptide may not be applied to retinopathy of prematurity if it suppresses all angiogenesis. Accordingly, the polypeptides and/or stem cells comprising an Xaa-Gly-Asp sequence may be very effectively used as a therapeutic agent for treating retinopathy of prematurity. Also, it seems that the polypeptide comprising an Xaa-Gly-Asp sequence enables the fundamental treatment of diabetic retinopathy by protecting a vessel structure at the beginning of the diabetic retinopathy. And, it seems that the polypeptide comprising an Xaa-Gly-Asp sequence suppresses growth of abnormal blood vessels in the age-related macular degeneration by aiding to normalize a vessel structure.

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Peptide Containing RGD Sequence

<400> SEQUENCE: 1

Arg Gly Asp Phe Val
1               5


<210> SEQ ID NO 2
<211> LENGTH: 10
<212> TYPE: PRT
<213> ORGANISM: Artificial Sequence
<220> FEATURE:
<223> OTHER INFORMATION: Peptide Containing RGD Sequence

<400> SEQUENCE: 2

Gly Phe Gly Arg Gly Asp Ser Pro Cys Ala
1               5                   10


<210> SEQ ID NO 3
<211> LENGTH: 5
<212> TYPE: PRT
<213> ORGANISM: Artificial Sequence
<220> FEATURE:
<223> OTHER INFORMATION: Peptide Containing RAD Sequence

<400> SEQUENCE: 3

Arg Ala Asp Phe Val
1               5
```

<210> SEQ ID NO 4
<211> LENGTH: 71
<212> TYPE: PRT
<213> ORGANISM: Artificial Sequence
<220> FEATURE:
<223> OTHER INFORMATION: Peptide Containing KGD Sequence

<400> SEQUENCE: 4

Glu Ala Gly Glu Glu Cys Asp Cys Gly Ser Pro Gly Asn Pro Cys Cys
1 5 10 15

Asp Ala Ala Thr Cys Lys Leu Arg Gln Gly Ala Gln Cys Ala Glu Gly
20 25 30

Leu Cys Cys Asp Gln Cys Arg Phe Met Lys Glu Gly Thr Ile Cys Arg
35 40 45

Ile Ala Lys Gly Asp Asp Leu Asp Asp Tyr Cys Asn Gly Ile Ser Ala
50 55 60

Gly Cys Pro Arg Asn Pro Phe
65 70

<210> SEQ ID NO 5
<211> LENGTH: 73
<212> TYPE: PRT
<213> ORGANISM: Artificial Sequence
<220> FEATURE:
<223> OTHER INFORMATION: Peptide containing RGD sequence

<400> SEQUENCE: 5

Glu Ala Gly Glu Glu Cys Asp Cys Gly Ala Pro Ala Asn Pro Cys Cys
1 5 10 15

Asp Ala Ala Thr Cys Lys Leu Arg Pro Gly Ala Gln Cys Ala Glu Gly
20 25 30

Leu Cys Cys Asp Gln Cys Arg Phe Met Lys Glu Gly Thr Ile Cys Arg
35 40 45

Met Ala Arg Gly Asp Asp Met Asp Asp Tyr Cys Asn Gly Ile Ser Ala
50 55 60

Gly Cys Pro Arg Asn Pro Phe His Ala
65 70

<210> SEQ ID NO 6
<211> LENGTH: 71
<212> TYPE: PRT
<213> ORGANISM: Artificial Sequence
<220> FEATURE:
<223> OTHER INFORMATION: Peptide containing RGD sequence

<400> SEQUENCE: 6

Glu Ala Gly Glu Glu Cys Asp Cys Gly Ser Pro Gly Asn Pro Cys Cys
1 5 10 15

Asp Ala Ala Thr Cys Lys Leu Arg Gln Gly Ala Gln Cys Ala Glu Gly
20 25 30

Leu Cys Cys Asp Gln Cys Arg Phe Met Lys Lys Gly Thr Val Cys Arg
35 40 45

Ile Ala Arg Gly Asp Asp Leu Asp Asp Tyr Cys Asn Gly Ile Ser Ala
50 55 60

Gly Cys Pro Arg Asn Pro Phe
65 70

<210> SEQ ID NO 7
<211> LENGTH: 73
<212> TYPE: PRT
<213> ORGANISM: Artificial Sequence <220> FEATURE:
<223> OTHER INFORMATION: Peptide containing RGD sequence

<400> SEQUENCE: 7

Glu Ala Gly Glu Glu Cys Asp Cys Gly Ser Pro Gly Asn Pro Cys Cys
1 5 10 15

Asp Ala Ala Thr Cys Lys Leu Arg Gln Gly Ala Gln Cys Ala Glu Gly
20 25 30

Leu Cys Cys Asp Gln Cys Arg Phe Met Lys Lys Gly Thr Val Cys Arg
35 40 45

Ile Ala Arg Gly Asp Asp Leu Asp Asp Tyr Cys Asn Gly Ile Ser Ala
50 55 60

Gly Cys Pro Arg Asn Pro Phe His Ala
65 70

<210> SEQ ID NO 8
<211> LENGTH: 58
<212> TYPE: PRT
<213> ORGANISM: Artificial Sequence
<220> FEATURE:
<223> OTHER INFORMATION: Peptide containing RGD sequence

<400> SEQUENCE: 8

Thr Cys Gln Leu Arg Pro Gly Ala Gln Cys Ala Ser Asp Gly Pro Cys
1 5 10 15

Cys Gln Asn Cys Gln Leu Arg Pro Ser Gly Trp Gln Cys Arg Pro Thr
20 25 30

Arg Gly Asp Cys Asp Leu Pro Glu Phe Cys Pro Gly Asp Ser Ser Gln
35 40 45

Cys Pro Pro Asp Val Ser Leu Gly Asp Gly
50 55

<210> SEQ ID NO 9
<211> LENGTH: 49
<212> TYPE: PRT
<213> ORGANISM: Artificial Sequence
<220> FEATURE:
<223> OTHER INFORMATION: Peptide containing RGD sequence

<400> SEQUENCE: 9

Glu Cys Glu Ser Gly Pro Cys Cys Arg Asn Cys Lys Phe Leu Lys Glu
1 5 10 15

Gly Thr Ile Cys Lys Arg Ala Arg Gly Asp Asp Met Asp Asp Tyr Cys
20 25 30

Asn Gly Leu Thr Cys Asp Cys Pro Arg Asn Pro His Lys Gly Pro Ala
35 40 45

Thr

<210> SEQ ID NO 10
<211> LENGTH: 68
<212> TYPE: PRT
<213> ORGANISM: Artificial Sequence
<220> FEATURE:
<223> OTHER INFORMATION: Peptide containing RGD sequence

<400> SEQUENCE: 10

Gly Lys Glu Cys Asp Cys Ser Thr Pro Glu Asn Pro Cys Cys Asp Ala
1 5 10 15

Ala Thr Cys Lys Leu Arg Pro Gly Ala Gln Cys Gly Glu Gly Leu Cys
20 25 30

-continued

```
Cys Glu Gln Cys Lys Phe Ser Arg Ala Gly Lys Ile Cys Arg Ile Pro
        35                  40                  45

Arg Gly Asp Met Pro Asp Asp Arg Cys Thr Gly Gln Ser Ala Asp Cys
    50                  55                  60

Pro Arg Tyr His
65
```

What is claimed is:

1. A method for treating a vascular-related disease in a subject in need thereof, which comprises administering to the subject a peptide consisting of the amino acid sequence of SEQ ID NO:8, wherein the vascular-related disease is edema caused by blood leakage of blood vessel walls, damages of blood vessels or abnormal angiogenesis.

2. The method according to claim 1, further comprising administering to the subject stem cells.

3. The method according to claim 2, wherein the stem cells have at least an ability to differentiate into vascular endothelial cells.

*4. A method for treating a vascular-related disease in a subject, comprising:*

*administering to the subject in need thereof a peptide selected from the group consisting of an amino acid sequence of SEQ ID NOs:1, 2, 5-7, 9, and 10,*

*wherein the vascular-related disease is edema or ischemia caused by blood leakage of blood vessel walls, damages of blood vessels, or abnormal angiogenesis.*

*5. The method according to claim 4, wherein the blood leakage of blood vessel walls, damages of blood vessels or abnormal angiogenesis is selected from the group consisting of blood leakage of blood vessel walls or damages of blood vessels associated with diabetic retinopathy, retinopathy of prematurity, age-related macular degeneration or glaucoma; diabetic foot ulcer; bedsore; chronic ulcer; and alopecia or trichopoliosis caused by failure in normal capillary formation.*

*6. The method according to claim 4, further comprising administering to the subject stem cells.*

*7. The method according to claim 6, wherein the stem cells have at least an ability to differentiate into vascular endothelial cells.*

*8. The method according to claim 4, further comprising administering to the subject VEGF or bFGF.*

*9. The method according to claim 7, wherein the vascular endothelial cells are each independently selected from the group consisting of an embryonic stem cell, a mesenchymal stem cell, and a hematopoietic stem cell.*

*10. The method according to claim 4, wherein the peptide is administered in a form of a pharmaceutical composition comprising a carrier.*

*11. The method according to claim 10, wherein the pharmaceutical composition is an injectable composition.*

*12. A method for treating a vascular-related disease in a subject, comprising:*

*administering to the subject in need thereof a peptide selected from the group consisting of an amino acid sequence of SEQ ID NO:8,*

*wherein the vascular-related disease is ischemia caused by blood leakage of blood vessel walls, damages of blood vessels, or abnormal angiogenesis.*

*13. The method according to claim 12, wherein the blood leakage of blood vessel walls, damages of blood vessels or abnormal angiogenesis is selected from the group consisting of blood leakage of blood vessel walls or damages of blood vessels associated with diabetic retinopathy, retinopathy of prematurity, age-related macular degeneration or glaucoma; diabetic foot ulcer; bedsore; chronic ulcer; and alopecia or trichopoliosis caused by failure in normal capillary formation.*

*14. The method according to claim 12, further comprising administering to the subject stem cells.*

*15. The method according to claim 14, wherein the stem cells have at least an ability to differentiate into vascular endothelial cells.*

*16. The method according to claim 12, further comprising administering to the subject VEGF or bFGF.*

*17. The method according to claim 15, wherein the vascular endothelial cells are each independently selected from the group consisting of an embryonic stem cell, a mesenchymal stem cell, and a hematopoietic stem cell.*

*18. The method according to claim 12, wherein the peptide is administered in a form of a pharmaceutical composition comprising a carrier.*

*19. The method according to claim 18, wherein the pharmaceutical composition is an injectable composition.*

* * * * *